(12) United States Patent
Bischof

(10) Patent No.: US 12,697,447 B2
(45) Date of Patent: Aug. 4, 2026

(54) INSUFFLATION DEVICE WITH INTELLIGENT CONTROL OF SMOKE EVACUATION

(71) Applicant: Novanta Medical GmbH, Berlin (DE)

(72) Inventor: Jan Bischof, Berlin (DE)

(73) Assignee: Novanta Medical GmbH, Berlin (DE)

( * ) Notice: Subject to any disclaimer, the term of this patent is extended or adjusted under 35 U.S.C. 154(b) by 445 days.

(21) Appl. No.: 17/257,887

(22) PCT Filed: Jul. 5, 2019

(86) PCT No.: PCT/DE2019/000176
§ 371 (c)(1),
(2) Date: May 10, 2021

(87) PCT Pub. No.: WO2020/007386
PCT Pub. Date: Jan. 9, 2020

(65) Prior Publication Data
US 2021/0267638 A1    Sep. 2, 2021

(30) Foreign Application Priority Data
Jul. 5, 2018    (DE) ..................... 10 2018 005 314.9

(51) Int. Cl.
*A61M 13/00*        (2006.01)
(52) U.S. Cl.
CPC .......... *A61M 13/003* (2013.01); *A61M 13/00* (2013.01); *A61M 2205/15* (2013.01); *A61M 2205/3334* (2013.01); *A61M 2205/75* (2013.01)

(58) Field of Classification Search
CPC .. A61M 13/00; A61M 13/003; A61M 13/006; A61M 2205/15;
(Continued)

(56) References Cited

U.S. PATENT DOCUMENTS

| | | | |
|---|---|---|---|
| 5,199,944 A | 4/1993 | Cosmescu | |
| 2015/0165146 A1* | 6/2015 | Bowman ............... | A61M 16/16 |
| | | | 128/203.14 |

(Continued)

FOREIGN PATENT DOCUMENTS

| | | |
|---|---|---|
| WO | 2004009167 A1 | 1/2004 |
| WO | 2015043570 A1 | 4/2015 |
| WO | 2018108200 A1 | 6/2018 |

*Primary Examiner* — Kami A Bosworth
*Assistant Examiner* — Avery Smale
(74) *Attorney, Agent, or Firm* — Kaplan Breyer Schwarz LLP

(57) ABSTRACT

The present invention relates to an insufflator with integrated smoke evacuation. By virtue of a novel control method of the evacuation volumetric flow rate, the following advantages are achieved. First, a reduction of the pressure in the cavity due to the evacuation is prevented. An empirically determined safety factor is determined, which results in the evacuation volumetric flow rate not exceeding the maximum possible insufflation volumetric flow rate. Second, the exchange volumetric flow rate is limited. It is limited such that the sum of the currently calculated leakage and the evacuation volumetric flow rate does not exceed a defined value. Thus, stress on the patient due to unnecessarily high exchange volumetric flow rates and the associated cooling and drying processes is prevented.

6 Claims, 1 Drawing Sheet

(58) Field of Classification Search
     CPC .. A61M 2205/3334; A61M 2205/3331; A61M
                2205/3341; A61M 2205/75; A61B 17/34;
                                            A61B 17/3474
     See application file for complete search history.

(56)                     References Cited

U.S. PATENT DOCUMENTS

| 2016/0101247 | A1* | 4/2016  | Zeyssig | A61M 13/003 |
|--------------|-----|---------|---------|-------------|
|              |     |         |         | 604/26      |
| 2017/0128127 | A1* | 5/2017  | Skalnyi | A61B 18/1485 |
| 2018/0133416 | A1  | 5/2018  | Silver  |             |
| 2018/0280634 | A1* | 10/2018 | O'Dea   | A61M 13/003 |
| 2018/0318165 | A1* | 11/2018 | Donda   | A61M 37/00  |
| 2019/0365417 | A1* | 12/2019 | Silver  | A61B 90/40  |

* cited by examiner

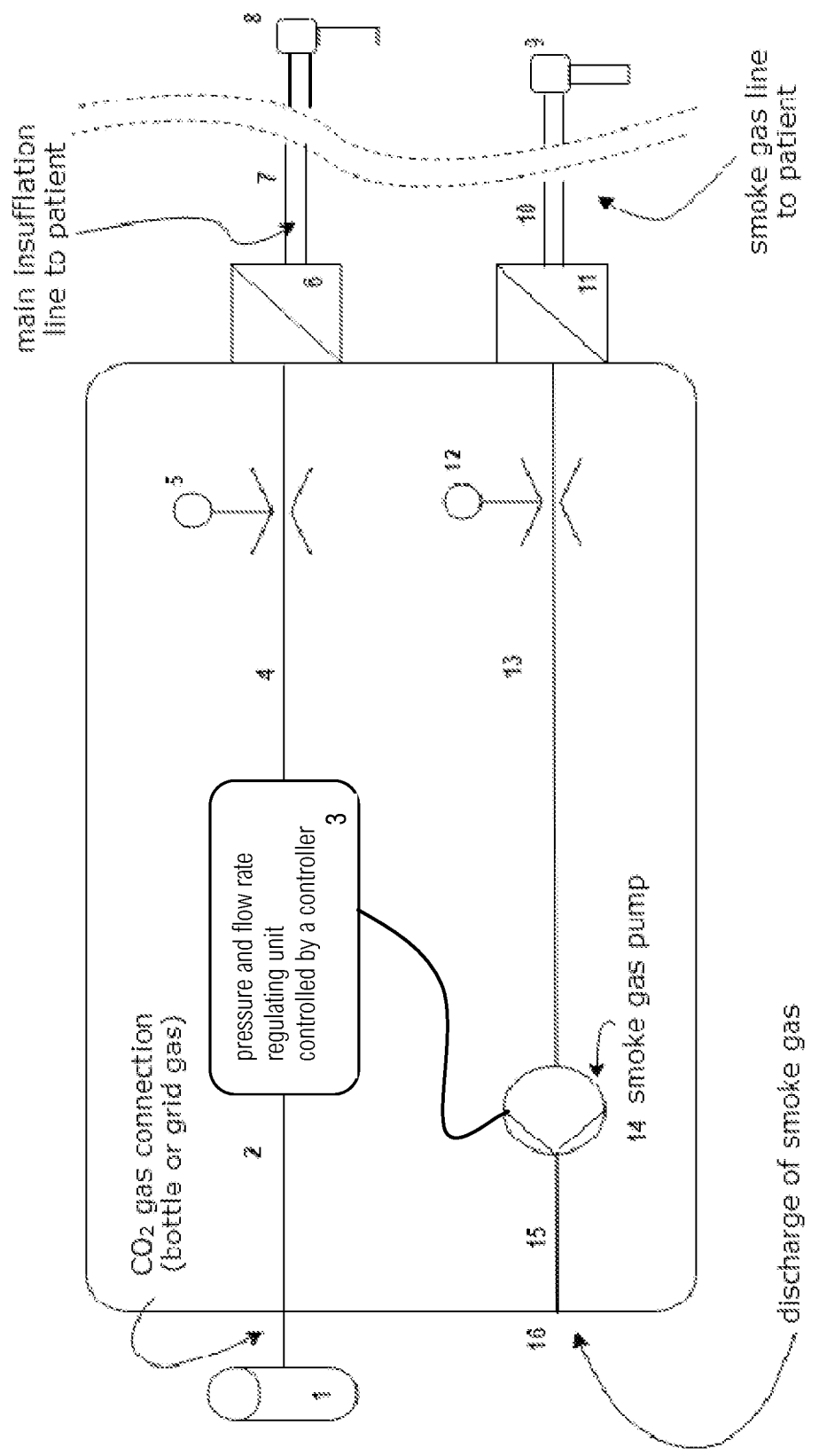

INSUFFLATION DEVICE WITH INTELLIGENT CONTROL OF SMOKE EVACUATION

CROSS-REFERENCE TO RELATED APPLICATION

This application is a National Stage entry of PCT/DE2019/000176, filed Jul. 5, 2019, which claims the benefit of German application No. 10 2018 005 314.9, filed Jul. 5, 2018, the contents of which are incorporated herein by reference.

The present invention relates to an insufflator with integrated smoke evacuation. A novel control method of the smoke evacuation enables to maintain the pressure in the patient even when leakages occur, and to limit the evacuation volumetric flow rate in case of high leakages.

BACKGROUND AND PRIOR ART

Insufflators offering the possibility of a simultaneous smoke evacuation are known from prior art (see, e.g., WO 2015/043570 A1). This insufflator comprises a hose, through which a medical gas is fed into a body cavity (e.g., an abdomen). The gas generates a positive pressure, which expands the body cavity, in order that there is sufficient space for visual inspections or therapeutic interventions. Through a second hose, the gas is evacuated again from the abdomen. In the case of therapeutic interventions by means of electrical surgery or laser, obnoxious smoke gases may be formed that are discharged and filtered by the insufflator via this second hose. The surgeon selects a desired target evacuation volumetric flow rate. The evacuation pump is regulated to the desired target evacuation volumetric flow rate. It is a problem when a larger leakage volumetric flow occurs or the resistance to flow of the insufflation line increases. In either case, the insufflator is not capable of insufflating the additionally necessary amount of $CO_2$. The consequence is that the cavity partially or completely collapses. In order to reduce this effect, according to the state of the art, the evacuation volumetric flow rate is limited or reduced in such situations. One possibility of implementation is to detect whether the measured pressure in the cavity differs from the desired target value, and then to reduce the maximum evacuation volumetric flow rate.

SUMMARY OF THE INVENTION

Most insufflators available on the market operate with a pulse-like method, in order to regulate the volumetric flow rate to be insufflated. Herein, insufflation phases alternate with so-called "measurement pauses". In the measurement pauses, the volumetric flow is turned off for a few hundred milliseconds, so that the pressure in the hose and the pressure in the cavity are balanced. Thereby, the insufflator can measure, by a pressure sensor in the insufflation line, for a short time the pressure in the cavity. Through the length of the insufflation phases, then the mean insufflation volumetric flow rate is controlled. When high volumetric flow rates are required, long insufflation phases are performed. In such a pulsed insufflation method, another possibility of regulating the evacuation flow is to use the length of an insufflation phase as a criterion for a decrease or an increase of the evacuation volumetric flow rate. When, for instance, the necessary length of the insufflation phase exceeds a predefined value, the smoke evacuation is reduced.

In the practice, it has been found that these two methods for limiting the evacuation volumetric flow rate have drawbacks. The most important drawback is that the pressure in the cavity must already have been reduced, in order that the evacuation volumetric flow rate is adjusted. This means that, when opening leakages, undesired pressure drops will occur, which can lead to delays in the surgery. An example is a larger leakage that occurs during the surgery.

Advanced insufflators are capable of generating insufflation volumetric flow rates of higher than 30 lpm. Thereby, even high leakages can be balanced, and simultaneously, a sufficient reserve for evacuation can be provided. This has, however, the following drawback: Even with high leakages, wherein, for surgeons, in fact, no evacuation would be required, the evacuation is not reduced. The evacuation continues with full evacuation power and stresses the patient by an additional cooling and drying process of the tissue. In order to reduce this drawback, in U.S. Pat. No. 5,199,944, a method is proposed, which only starts the smoke evacuation when smoke gases are generated. Further state of the art follows from the document US 2018/0133416 A1. In the present patent document, an alternative method is described.

DESCRIPTION OF THE DRAWINGS

FIG. 1 shows an insufflator providing gas to a patient cavity during minimally invasive surgery.

DETAILED DESCRIPTION OF THE INVENTION

The present invention relates to an insufflator for minimally invasive surgery, including a) a pressure and flow rate-regulating unit equipped with a proportional valve, a pressure sensor and a flow rate measurement device, b) a supply line with an optional filter and connection to a first trocar, c) a second trocar with an evacuation hose and an optional filter, connected to an evacuation device with controllable evacuation power, d) an optional flow rate measurement device in the evacuation line, e) an electronic or mechanical regulating unit, and f) a novel method for adjustment of the evacuation volumetric flow rate.

With small leakages, the insufflator is operated, as is described in the state of the art (WO 2015/043570 A1). The gas connection (1) leads via a line (2) to the pressure and flow rate-regulating unit (3) of the supply line (4). In the pressure and flow rate unit (3) is provided a pressure sensor, in order to monitor the pressure in the line. Furthermore, a flow rate-measurement device (5) is mounted for volumetric flow rate measurement behind the pressure and flow rate unit (3). Further, a filter for protection of the patient is provided (6). The supply line (7) terminates in a first trocar (8) that can fill the body cavity with gas. The insufflator further includes a second hose (10) serving as an evacuation hose. A second trocar (9) introduced into the body cavity (9) is connected by means of this evacuation hose (10) to the insufflator. The evacuation hose, too, comprises an optional filter (11) and leads via a line (13) to an evacuation pump (14). The evacuation power of the evacuation pump is controllable. Via a line (15), the smoke is discharged from the insufflator (16). The evacuation volumetric flow rate can be measured either through the optional flow rate sensor (12) or can be determined by the power of the evacuation pump (14). Different from insufflators of prior art, the insufflator according to the invention comprises a novel intelligent control method of the evacuation volumetric flow rate.

A controller is operatively connected to the pressure and flow rate regulating unit and the evacuation device. The controller controls the evacuation device so as to adjust the evacuation volumetric flow rate based at least in part on a defined maximum volumetric flow rate and a determined leakage volumetric flow rate.

The novel method for adjustment of the evacuation volumetric flow rate comprises the following steps:

(a) Determination of the current maximum insufflation power: The maximum insufflation volumetric flow rate is mainly dependent on the resistance to flow of the used trocar-instrument combination and the maximum pressure. This pressure is typically set to a value, which leads to a still acceptable risk for the patient and must not further be increased. In order to determine the maximum possible insufflation volumetric flow rate, different methods can be used. For instance, an algorithm can be used, which determines the characteristic of the trocar instrument. Alternatively, mathematical models, such as the Kalman filter or Luenberger observer, can be used to determine the maximum insufflation power.

(b) Determination of the current leakage volumetric flow rate $q_{Leakage}$: The leakage, too, can be estimated by a mathematical model. Alternatively, the mean leakage can also approximately be calculated by a subtraction of the mean evacuation volumetric flow rate from the mean insufflation volumetric flow rate.

(c) Calculation of the maximum possible evacuation volumetric flow rate $q_{Evacuation,max}$: By subtraction of the determined leakage from the maximum insufflation flow rate and subsequent multiplication with a safety factor between 0 and 1, which defines, with which load the insufflator ideally is stressed. The value is typically between 0.6 and 0.9.

(d) Verification whether a maximum exchange flow is exceeded:

In order to prevent that a high evacuation volumetric flow rate remains adjusted, even when in this situation leakages cause already a high gas exchange, the evacuation volumetric flow rate is additionally limited. For this purpose, a maximum exchange volumetric flow rate $q_{Exchange,max}$ is defined. Typical values for $q_{Exchange,max}$ are between 10 and 20 lpm. The value either can be adjusted via a graphical interface or is fixedly configured in the insufflator or adjusted by the software. The maximum evacuation volumetric flow rate $q_{Exchange,max}$ is then limited such that the equation $q_{Evacuation,max}+q_{Leakage}\leq q_{Exchange,max}$ is satisfied. In other words: The sum of the maximum evacuation volumetric flow rate and the estimated leakage must not be larger than a defined value for $q_{Exchange,max}$.

(d) If the evacuation volumetric flow rate adjusted by the surgeon is larger than the calculated maximum evacuation volumetric flow rate $q_{Exchange,max}$, the target evacuation volumetric flow rate is limited to the maximum allowed evacuation volumetric flow rate $q_{Evacuation,max}$.

(e) The calculation is cyclically repeated (for instance every second), in order that the maximum allowed evacuation volumetric flow rate can continuously be adapted to changes in leakage or changes in the trocar-instrument combination.

A calculation example for illustration:

(a) The characteristic of the trocar-instrument combination is determined as $q_{Instrument}=0.2$ lpm/mmHg$\times p_{Hose}$ with the volumetric flow rate $q_{Instrument}$ and the pressure in the hose $p_{Hose}$. The pressure for acceptable safety may be 100 mmHg. Then follows a maximum volumetric flow rate of $q_{max}=0.2$ lpm/mmHg$\times 100$ mmHg$=20$ lpm.

(b) The leakage is estimated by an observer or another method to be 10 lpm.

(c) The safety factor is selected as 0.8. Then follows a maximum evacuation flow $q_{Evacuation,max}=20$ lpm$\times 0.8-10$ lpm$=6$ lpm.

(d) When the surgeon has selected an evacuation volumetric flow rate of for instance 8 lpm, this is reduced to the maximum evacuation volumetric flow rate $q_{Evacuation,max}=6$ lpm, in order to prevent that the pressure is reduced too much by the selected evacuation.

(e) When the maximum exchange volumetric flow rate $q_{Exchange,max}$ was configured to be 18 lpm, the condition $q_{Evacuation,max}+q_{Leakage}\leq q_{Exchange,max}$ is satisfied. Thus, there is no further reduction of the evacuation volumetric flow rate by the maximum exchange volumetric flow rate. When the maximum exchange volumetric flow rate $q_{Exchange,max}$ would have been configured to be 12 lpm, the evacuation volumetric flow rate would be reduced to 2 lpm.

(f) The calculation is cyclically repeated, and when for instance the maximum insufflation power $q_{max}$ is reduced, $q_{Evacuation,max}$ is also adjusted.

The invention claimed is:

1. An insufflator for providing gas to a patient cavity during minimally invasive surgery, comprising:

a) a gas connection configured to receive a gas supply and provide the gas supply to a pressure and flow rate regulating unit equipped with a flow rate measuring unit, a proportional valve and a pressure sensor, the pressure and flow rate regulating unit configured to be controlled by a controller;

b) a supply line configured to receive the gas supply from the pressure and flow rate regulating unit, the supply line connected to a first trocar for providing pressurized gas to the patient cavity;

c) a second trocar connected to an exhaust line which is operatively connected to an evacuation device configured to remove flue gas from the patient cavity;

d) a second flow rate measuring unit operatively positioned in a flow path between the evacuation device and the second trocar, the second flow rate measuring unit configured to measure an evacuation volumetric flow rate;

e) the controller operatively connected to the pressure and flow rate regulating unit and the evacuation device; wherein the controller is configured to control the evacuation device so as to adjust the evacuation volumetric flow rate based at least in part on a defined maximum volumetric supply flow rate and a determined leakage volumetric flow rate;

wherein the insufflator is configured to:

a. determine a maximum possible insufflation volumetric flow rate based on a flow resistance characteristic, wherein the maximum possible insufflation volumetric flow rate is determined using a mathematical model that is a Kalman filter or a Luenberger observer;

b. determine the determined leakage volumetric flow rate, wherein the determined leakage volumetric flow rate is determined by a mathematical observer model;

c. multiply the maximum possible insufflation volumetric flow rate with a safety factor to determine a reduced maximum insufflation volumetric flow rate, d. determine a maximum allowed evacuation volumet-
      ric flow rate by subtraction of the determined leakage
      volumetric flow rate from the reduced maximum
      insufflation volumetric flow rate;
   e. define the defined maximum volumetric supply flow
      rate, being the reduced maximum insufflation volu-
      metric flow rate;
   f. determine whether the defined maximum volumetric
      supply flow rate is exceeded based on the maximum
      allowed evacuation volumetric flow rate and the
      determined leakage volumetric flow rate; and
   g. limit and reduce the maximum allowed evacuation
      volumetric flow rate if the defined maximum volu-
      metric supply flow rate is exceeded.

2. The insufflator as recited in claim 1, wherein the pressure sensor is positioned within the pressure and flow rate regulating unit.

3. The insufflator according to claim 1, wherein the safety factor used for determining the reduced maximum insufflation volumetric flow rate is between about 0.6 and 0.9.

4. The insufflator according to claim 1, wherein the defined maximum volumetric supply flow rate is between about 10 and 20 lpm.

5. The insufflator according to claim 1, wherein the insufflator is further configured to cyclically repeat at least some of a-g in order that the maximum allowed evacuation volumetric flow rate can continuously be adapted to changes in leakage or changes in the flow resistance characteristic.

6. The insufflator according to claim 5, wherein the insufflator is further configured to cyclically repeat at least some of a-g every second.

\* \* \* \* \*